United States Patent
Sarkar et al.

(10) Patent No.: US 12,084,548 B2
(45) Date of Patent: *Sep. 10, 2024

(54) CARBOXYLIC ACID FUNCTIONAL CROSS-LINKED SILICONE COMPOSITIONS

(71) Applicant: Momentive Performance Materials Inc., Waterford, NY (US)

(72) Inventors: Alok Sarkar, Bangalore (IN); Benjamin Falk, Yorktown Heights, NY (US); Ashitha Kandikkal, Bangalore (IN); Debarshi Dasgupta, Bangalore (IN)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 202 days.

This patent is subject to a terminal disclaimer.

(21) Appl. No.: 17/321,250

(22) Filed: May 14, 2021

(65) Prior Publication Data

US 2021/0355283 A1 Nov. 18, 2021

Related U.S. Application Data

(60) Provisional application No. 63/026,404, filed on May 18, 2020.

(51) Int. Cl.
| | | |
|---|---|---|
| *C08G 77/24* | (2006.01) |
| *A61K 8/893* | (2006.01) |
| *C08G 77/00* | (2006.01) |
| *C08G 77/06* | (2006.01) |
| *C08G 77/12* | (2006.01) |
| *C08G 77/18* | (2006.01) |

(52) U.S. Cl.
CPC ............ *C08G 77/12* (2013.01); *A61K 8/893* (2013.01); *C08G 77/06* (2013.01); *C08G 77/18* (2013.01); *C08G 77/24* (2013.01); *C08G 77/70* (2013.01)

(58) Field of Classification Search
CPC .......... C08G 77/14; C08G 77/50; C08L 83/14
See application file for complete search history.

(56) References Cited

U.S. PATENT DOCUMENTS

| | | | |
|---|---|---|---|
| 3,159,601 A | 12/1964 | Ashby | |
| 3,159,662 A | 12/1964 | Ashby | |
| 3,220,972 A | 11/1965 | Lamoreaux | |
| 3,715,334 A | 2/1973 | Karstedt | |
| 3,775,452 A | 11/1973 | Karstedt et al. | |
| 3,814,730 A | 6/1974 | Karstedt et al. | |
| 4,987,169 A | 1/1991 | Kuwata et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |
| 6,423,322 B1 | 7/2002 | Fry | |
| 2004/0147670 A1* | 7/2004 | Hupfield | C08J 3/09 524/588 |
| 2010/0190871 A1* | 7/2010 | Araki | A61K 8/891 514/772.3 |
| 2010/0247460 A1* | 9/2010 | Lin | A61Q 15/00 556/400 |
| 2017/0065514 A1* | 3/2017 | Crofoot | A61Q 5/02 |

OTHER PUBLICATIONS

Sarkar, A., et al., "Evidence of Cooperativity among van der Waals Interactions in Segmented Polysiloxane," *Macromolecules* 51(22):9354-9359, American Chemical Society, United States (Nov. 2018).
Speier, J. L., "Homogeneous Catalysis of Hydrosilation by Transition Metals," *Advances in Organometallic Chemistry* 17:407-447, Elsevier, Netherlands (1979).
Co-pending U.S. Appl. No. 17/321,257, inventors Sarkar, A., et al., filed on May 14, 2021 (Not yet Published).
International Search Report and Written Opinion for International Application No. PCT/US2021/032570, European Patent Office, Netherlands, mailed Aug. 27, 2021, 11 pages.
International Search Report and Written Opinion for International Application No. PCT/US2021/032567, European Patent Office, Netherlands, mailed on Aug. 27, 2021, 12 pages.
Sarkar, A., et al., "Evidence of Cooperativity among van der Waals Interactions in Segmented Polysiloxane," Macromolecules 51(22):9354-9359, American Chemical Society, Washington, DC, US (2018).

* cited by examiner

*Primary Examiner* — Margaret G Moore
(74) *Attorney, Agent, or Firm* — Sterne, Kessler Goldstein & Fox P.L.L.C.

(57) ABSTRACT

The present disclosures are directed to compositions comprising a polymer having branched silicone substituted by at least one alkylcarboxy group in a free or salt form and cross-linked with an alkyl functional cross-linker, which has the benefits of compatibility with hydrophilic ingredients and particulates in personal care components and the resultant personal care applications.

26 Claims, No Drawings

CARBOXYLIC ACID FUNCTIONAL CROSS-LINKED SILICONE COMPOSITIONS

BACKGROUND

Field

This invention relates to compositions comprising a polymer having branched silicone substituted by at least one alkylcarboxy group in a free or salt form and cross-linked with an alkyl functional cross-linker. In one aspect, personal care compositions containing such polymers are provided herein.

Background

Silicone gels are commonly added in a variety of personal care formulations to enhance their aesthetics with respect to sensory, texture, rheology and optical performance. However, traditional silicone gels have limited versatility in terms of compatibility with polar solvents such as hydrocarbon oils, plant-based oils, glycerin and water. Moreover, most of these gels often fail to retain their texture and rheological benefits at lower dosage. Therefore, there exists a need for a silicone gel composition with improved compatibility, texture and rheological performance.

BRIEF SUMMARY OF THE DISCLOSURE

Compositions comprising a polymer having branched silicone substituted by at least one alkylcarboxy group in a free or salt form and cross-linked with an alkyl functional cross-linker, wherein an average number of alkylcarboxy substitutions per silicone is between 1 and 60 and an average number of crosslinks between branched silicones being between 1 and 30 are described herein. In some aspects, the average number of alkylcarboxy substitutions per silicone is between 1 and 15. In some aspects, the average number of alkylcarboxy substitutions per silicone is between 1 and 12. In some aspects, the average number of crosslinks between branched silicones is between 1 and 15. In some aspects, the average number of crosslinks between branched silicones is between 1 and 12.

Compositions of the disclosure exhibit enhanced hydrophilic compatibility, structuring and rheological performance compared to randomly distributed carboxy moieties prepared using linear hydride as cross-linker.

In some aspects, the polymer is prepared by a method comprising
(a) reacting
i. a Si—H functional compound of formula (I):

$$[SiO_{4/2}]_a[R^1SiO_{3/2}]_b[R^2MeSiO_{2/2}]_c[HMeSiO_{2/2}]_d[R^3Me_2SiO_{1/2}]_e[HMe_2SiO_{1/2}]_f \qquad (I)$$

wherein
$R^1$ is hydrogen, an aliphatic, aromatic, or fluoro monovalent hydrocarbon having from 1 to 60 carbon atoms;
$R^2$ and $R^3$ are each an aliphatic, aromatic, or fluoro monovalent hydrocarbon having from 1 to 60 carbon atoms; and
$a \geq 0$, $b \geq 0$, $a+b \geq 1$, $c \geq 0$, $d \geq 0$, $e \geq 0$, $f \geq 1$, and $d+f \geq 2$;
ii. a carboxy functional olefin of formula (II):

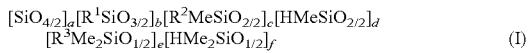

(II)

wherein
R' is hydrogen or —Si(R$^a$)$_3$ wherein R$^a$ is an aliphatic monovalent hydrocarbon;
n is $0 \leq n \leq 30$; and
iii. a silicone based alkenyl functional cross-linker of formula (III) and/or a non-silicone based alkenyl functional cross-linker of formula (IV):

$$M^1_{a'}M^2_{b'}D^1_{c'}D^2_{d'}T^1_{e'}T^2_{f'}Q_{g'}, \qquad (III)$$

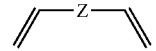

(IV)

wherein:
$M^1 = R^4R^5R^6SiO_{1/2}$;
$M^2 = R^7R^8R^9SiO_{1/2}$;
$D^1 = R^{10}R^{11}SiO_{2/2}$;
$D^2 = R^{12}R^{13}SiO_{2/2}$;
$T^1 = R^{14}SiO_{3/2}$;
$T^2 = R^{15}SiO_{3/2}$;
$Q = SiO_{4/2}$;
wherein
$R^5$, $R^6$, $R^7$, $R^8$, $R^9$, $R^{11}$, $R^{12}$, $R^{13}$, and $R^{15}$ are independently an aliphatic, aromatic, or fluoro monovalent hydrocarbon having from 1 to 60 carbon atoms;
$R^4$, $R^{10}$, and $R^{14}$ are each a monovalent radical containing at least one terminal olefin bond;
a', b', c', d', e', f' and g' are independently zero or a positive integer, such that $2 \leq a'+b'+c'+d'+e'+f'+g' \leq 6000$ and when a'+c'+e'=2, d+f>2 or when d+f=2, a'+c'+e'>2; and
Z is an aliphatic hydrocarbon with 1 to 60 carbon atoms; and
(b) deprotecting the reaction product of step (a) to replace the —Si(R$^a$)$_3$ group with a hydrogen.

The polymer can be prepared by mixing the components in any order. Additionally, each component can be added simultaneously or sequentially, or as batch or semi-batch preparations.

The disclosure also relates to methods for preparing the polymer comprising reacting:
i. a Si—H functional compound of formula (I):

$$[SiO_{4/2}]_a[R^1SiO_{3/2}]_b[R^2MeSiO_{2/2}]_c[HMeSiO_{2/2}]_d[R^3Me_2SiO_{1/2}]_e[HMe_2SiO_{1/2}]_f \qquad (I)$$

wherein
$R^1$ is hydrogen or an aliphatic, aromatic, or fluoro monovalent hydrocarbon having from 1 to 60 carbon atoms;
$R^2$ and $R^3$ are each an aliphatic, aromatic, or fluoro monovalent hydrocarbon having from 1 to 60 carbon atoms; and
$a \geq 0$, $b \geq 0$, $a+b \geq 1$, $c \geq 0$, $d \geq 0$, $e \geq 0$, $f \geq 1$, and $d+f \geq 2$;
ii. a carboxy functional olefin of formula (II):

(II)

wherein
R' is hydrogen or —Si(R$^a$)$_3$ wherein IV is an aliphatic monovalent hydrocarbon;
n is $0 \leq n \leq 30$; and
iii. a silicone based alkenyl functional cross-linker of formula (III) and/or a non-silicone based alkenyl functional cross-linker of formula (IV):

$$M^1{}_{a'}M^2{}_{b'}D^1{}_{c'}D^2{}_{d'}T^1{}_{e'}T^2{}_{f'}Q_{g'}, \quad \text{(III)}$$

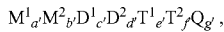 (IV)

wherein:
$M^1 = R^4R^5R^6SiO_{1/2}$;
$M^2 = R^7R^8R^9SiO_{1/2}$;
$D^1 = R^{10}R^{11}SiO_{2/2}$;
$D^2 = R^{12}R^{13}SiO_{2/2}$;
$T^1 = R^{14}SiO_{3/2}$;
$T^2 = R^{15}SiO_{3/2}$; and
$Q = SiO_{4/2}$;
wherein
$R^5$, $R^6$, $R^7$, $R^8$, $R^9$, $R^{11}$, $R^{12}$, $R^{13}$, and $R^{15}$ are independently an aliphatic, aromatic, or fluoro monovalent hydrocarbon having from 1 to 60 carbon atoms;
$R^4$, $R^{10}$, and $R^{14}$ are each a monovalent radical containing at least one terminal olefin bond;
a', b', c', d', e', f' and g' are independently zero or a positive integer, such that $2 \le a'+b'+c'+d'+e'+f'+g' \le 6000$ and when a'+c'+e'=2, d+f>2 or when d+f=2, a'+c'+e'>2; and
Z is an aliphatic hydrocarbon with 1 to 60 carbon atoms.

The polymer can be prepared by mixing the components in any order. Additionally, each component can be added simultaneously or sequentially, or as batch or semi-batch preparations.

The disclosure further relates to preparing a polymer, comprising deprotecting a reaction product of i. a Si—H functional compound of formula (I):

$$[SiO_{4/2}]_a[R^1SiO_{3/2}]_b[R^2MeSiO_{2/2}]_c[HMeSiO_{2/2}]_d[R^3Me_2SiO_{1/2}]_e[HMe_2SiO_{1/2}]_f \quad \text{(I)}$$

wherein
$R^1$ is hydrogen, an aliphatic, aromatic, or fluoro monovalent hydrocarbon having from 1 to 60 carbon atoms;
$R^2$ and $R^3$ are each an aliphatic, aromatic, or fluoro monovalent hydrocarbon having from 1 to 60 carbon atoms; and
$a \ge 0$, $b \ge 0$, $a+b \ge 1$, $c \ge 0$, $d \ge 0$, $e \ge 0$, $f > 1$, and $d+f \ge 2$;

ii. a carboxy functional olefin of formula (II):

 (II)

wherein
R' is hydrogen or —Si(R$^a$)$_3$ wherein R$^a$ is an aliphatic monovalent hydrocarbon;
n is $0 \le n \le 30$; and iii. a silicone based alkenyl functional cross-linker of formula (III) and/or a non-silicone based alkenyl functional cross-linker of formula (IV):

$$M^1{}_{a'}M^2{}_{b'}D^1{}_{c'}D^2{}_{d'}T^1{}_{e'}T^2{}_{f'}Q_{g'}, \quad \text{(III)}$$

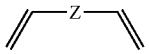 (IV)

wherein:
$M^1 = R^4R^5R^6SiO_{1/2}$;
$M^2 = R^7R^8R^9SiO_{1/2}$;
$D^1 = R^{10}R^{11}SiO_{2/2}$;
$D^2 = R^{12}R^{13}SiO_{2/2}$;
$T^1 = R^{14}SiO_{3/2}$;
$T^2 = R^{15}SiO_{3/2}$; and
$Q = SiO_{4/2}$;
wherein
$R^5$, $R^6$, $R^7$, $R^8$, $R^9$, $R^{11}$, $R^{12}$, $R^{13}$, and $R^{15}$ are independently an aliphatic, aromatic, or fluoro monovalent hydrocarbon having from 1 to 60 carbon atoms;
$R^4$, $R^{10}$, and $R^{14}$ are each a monovalent radical containing at least one terminal olefin bond;
a', b', c', d', e', f' and g' are independently zero or a positive integer, such that $2 \le a'+b'+c'+d'+e'+f'+g' \le 6000$ and when a'+c'+e'=2, d+f>2 or when d+f=2, a'+c'+e'>2; and
Z is an aliphatic hydrocarbon with 1 to 60 carbon atoms.

The polymer can be prepared by mixing the components in any order. Additionally, each component can be added simultaneously or sequentially, or as batch or semi-batch preparations.

In some aspects, the method further comprises deprotecting the reaction product to replace the —Si(R$^a$)$_3$ group with a hydrogen.

In some aspects, the reaction between the Si—H functional compound of formula (I), the carboxy functional olefin of formula (II) and the alkenyl functional cross-linker of formula (III) and/or (IV) occurs in the presence of at least one precious metal catalyst selected from the group consisting of a rhodium, ruthenium, palladium, osmium, iridium, iron, and platinum catalyst. In some aspects, at least one of the platinum catalysts is selected from the group consisting of (PtCl2Olefin), H(PtCl3Olefin), platinic chloride, chloroplatinic acid, bis(acetylacetonato)platinum, (η5-Cyclopentadienyl)trialkylplatinum, Pt$_2$(dba)$_3$, Pt$_2$(dvs)$_3$, Pt(OAc)$_2$, Pt(acac)$_2$, Na$_2$PtCl$_6$, K$_2$PtCl$_6$, platinum carbonate, platinum nitrate, 1,5-cyclooctadienedimethylplatinum(II), platinum perchlorate, amine complexes of the platinum ammonium hexachloropalladate(IV), a cyclopropane complex of platinum chloride, and a complex formed from chloroplatinic acid.

In some aspects, $R^1$ is an aliphatic, aromatic, or fluoro monovalent hydrocarbon. In some aspects, $R^1$ is a $C_1$-$C_{30}$ monovalent hydrocarbon. In some aspects, $R^1$ is a $C_1$-$C_{18}$ monovalent hydrocarbon. In some aspects, $R^1$ is phenyl.

In some aspects, one or more of $R^2$ and $R^3$ is a $C_1$-$C_{30}$ monovalent hydrocarbon. In some aspects, the one or more of $R^2$ and $R^3$ is a $C_1$-$C_{18}$ monovalent hydrocarbon.

In some aspects, $R^a$ is a $C_1$-$C_{12}$ group. In some aspects, $R^a$ is a $C_1$-$C_8$ group. In some aspects, $R^a$ is selected from the group consisting of methyl, ethyl, propyl, butyl, pentyl, hexyl, and heptyl. In some aspects, IV is methyl.

In some aspects, one or more of $R^5$, $R^6$, $R^7$, $R^8$, $R^9$, $R^{11}$, $R^{12}$, $R^{13}$, and $R^{15}$ is a $C_1$-$C_{30}$ monovalent hydrocarbon. In some aspects, the one or more of $R^5$, $R^6$, $R^7$, $R^8$, $R^9$, $R^{11}$, $R^{12}$, $R^{13}$, and $R^{15}$ is an aliphatic monovalent hydrocarbon. In some aspects, the one or more of $R^5$, $R^6$, $R^7$, $R^8$, $R^9$, $R^{11}$, $R^{12}$, $R^{13}$, and $R^{15}$ is selected from the group consisting of methyl, ethyl, n-propyl, isopropyl, n-butyl, isobutyl, tert-butyl, n-pentyl, isopentyl, neo-pentyl, tert-pentyl, hexyl, heptyl, octyl, nonyl, decyl, and cycloalkyl. In some aspects, the one or more of $R^5$, $R^6$, $R^7$, $R^8$, $R^9$, $R^{11}$, $R^{12}$, $R^{13}$, and $R^{15}$ is selected from the group consisting of n-hexyl, n-heptyl, n-octyl, isooctyl, 2,2,4-trimethylpentyl, n-nonyl, n-decyl, cyclopentyl, cyclohexyl, cycloheptyl, and methylcyclohexyl.

In some aspects, one or more of $R^5$, $R^6$, $R^7$, $R^8$, $R^9$, $R^{11}$, $R^{12}$, $R^{13}$, and $R^{15}$ is an aromatic monovalent hydrocarbon. In some aspects, the one or more of $R^5$, $R^6$, $R^7$, $R^8$, $R^9$, $R^{11}$, $R^{12}$, $R^{13}$, and $R^{15}$ is selected from the group consisting of phenyl, naphthyl, o-tolyl, m-tolyl, p-tolyl, xylyl, ethylphenyl, and benzyl.

In some aspects, one or more of $R^5$, $R^6$, $R^7$, $R^8$, $R^9$, $R^{11}$, $R^{12}$, $R^{13}$, and $R^{15}$ is a fluoro monovalent hydrocarbon. In some aspects, the one or more of $R^5$, $R^6$, $R^7$, $R^8$, $R^9$, $R^{11}$, $R^{12}$, $R^{13}$, and $R^{15}$ is a $C_1$-$C_{18}$ monovalent hydrocarbon.

In some aspects, a', b', c', d', e', f', and g' are $2 \leq a'+b'+c'+d'+e'+f'+g' \leq 4000$. In some aspects, a', b', c', d', e', f', and g' are $2 \leq a'+b'+c'+d'+e'+f'+g' \leq 2000$. In some aspects, a', c', and e' are $2 \leq a'+c'+e' \leq 120$. In some aspects, a', c', and e' are $2 \leq a'+c'+e' \leq 100$. In some aspects, a'=2, d'=75-600, and b'=c'=e'=f'=g'=0

In some aspects, a=10, b=c=d=e=0, f=12, and n=8. In some aspects, a=0, b=1, c=d=e=0, f=3, and n=8.

In some aspects, Z is $-(CHR^{16})_m-$ or $-(CH_2CHR^{17}O)_k-$, wherein m and k are positive integers, such that $1 \leq m \leq 60$ and $1 \leq k \leq 500$, and $R^{16}$ and $R^{17}$ are independently hydrogen or monovalent hydrocarbon having from 1 to 60 carbon atoms. In some aspects, Z is $-(CHR^{16})_m-$, m is 1-30, and $R^{16}$ is from 1 to 30 carbon atoms. In some aspects, Z is $-(CHR^{16})_m-$, m is 1-18, and $R^{16}$ is from 1 to 20 carbon atoms. In some aspects, Z is $-(CH_2CHR^{17}O)_k-$, k is 1-250, and $R^{17}$ is from 1 to 30 carbon atoms. In some aspects, Z is $-(CH_2CHR^{17}O)_k-$, k is 1-100, and $R^{17}$ is from 1 to 20 carbon atoms.

In some aspects, the polymer is in a free form. In some aspects, the polymer is in a salt form. In some aspects, a cation of the salt form is independently selected from alkali metals, alkaline earth metals, transition metals, rare earth metals, metals, metal complexes, quaternary ammonium and phosphonium groups, organic cations, alkyl cations, cationic hydrocarbons, cationic polymers, or zwitterions.

The disclosure also relates to a product prepared by any of the methods described herein.

The disclosure additionally relates to personal care compositions comprising (a) a composition or product described herein; and (b) one or more personal care components.

In some aspects, the one or more personal care components are selected from the group consisting of a humectant, emollient, moisturizer, pigment, colorant, fragrance, biocide, preservative, antioxidant, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, and thickening agent. In some aspects, the one or more emollients is selected from the group consisting of triglyceride esters, wax esters, alkyl or alkenyl ester of fatty acids, polyhydric alcohol esters, and mixtures thereof. In some aspects, the one or more personal care components is a silicone oil, an organic oil, or mixtures thereof.

The disclosure further relates to a personal care application comprising a personal care component described herein, wherein the personal care application is selected from the group consisting of a deodorant, antiperspirant, antiperspirant/deodorant, shaving product, skin lotion, moisturizer, toner, bath product, cleansing product, hair care product, manicure product, protective cream, and color cosmetic.

DETAILED DESCRIPTION

Definitions and Abbreviations

As used above, and throughout the description, the following terms, unless otherwise indicated, shall be understood to have the following meanings.

Unless stated otherwise, the terms "a" and "an" and "the" and similar references used in the context of describing a particular aspect of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein.

The term "carboxy" means the radical $-C(O)O-$. It is noted that compounds described herein containing carboxy moiety can include protected derivatives thereof, i.e., where the oxygen is substituted with a protecting group. Suitable protecting groups for carboxy moieties include trimethylsilyl, triisopropylsilyl, tert-butyldimethylsilyl, benzyl, tert-butyl, methyl, ethyl, and the like. The term "carboxyl" means $-COOH$.

The term "polymer" means a substance, chemical compound or mixture of compounds, that has a molecular structure consisting chiefly or entirely of a large number of similar units (e.g., monomer units) bonded together.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The term "aliphatic monovalent hydrocarbon" as used herein, means hydrocarbon which is completely saturated and is not aromatic. For example, suitable aliphatic groups include linear alkyl groups. A "fluoro monovalent hydrocarbon" means a completely saturated hydrocarbon that is substituted with a fluoro atom.

The term "hydrocarbon" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group. Examples of "alkyl" groups include methyl, ethyl, isopropyl, and the like.

The term "aromatic" refer to an optionally substituted $C_{6-14}$ aromatic hydrocarbon moiety comprising one to three aromatic rings. In at least one aspect, the aromatic group is a $C_{6-10}$ aryl group. Aromatic groups include, without limitation, phenyl. The term "aromatic" can be used interchangeably with the terms "aryl group," "aryl ring," and "aryl."

In describing the products as a reaction product of initial materials, reference is made to the initial species recited and it is to be noted that additional materials can be added to the initial mixture of synthetic precursors. These additional materials can be reactive or non-reactive. The defining characteristic is that the reaction product can be obtained from the reaction of at least the components listed as disclosed. Non-reactive components can be added to the reaction mixture as diluents or to impart additional properties unrelated to the properties of the composition prepared as a reaction product. Thus, for example particulate solids, such as pigments, can be dispersed into the reaction mixture, before, during, or after the reaction to produce a reaction product composition that additionally comprises the non-reactive component. Additional reactive components can also be added. Such components can react with the initial reactants or they can react with the reaction product. The phrase "reaction product" is intended to include those possibilities, as well as including the addition of non-reactive components.

The expression "shearing" as used herein means the silicone composition can be further processed to adjust the viscosity and sensory feel of the composition. This can be achieved, for example, by subjecting the composition to a moderate to high shearing force.

As used herein, the term "non-aqueous hydroxylic organic compound" or "non-aqueous hydroxylic solvent" means hydroxyl containing organic compounds such as, but not limited to, alcohols, glycols, polyhydric alcohols and polymeric glycols and mixtures thereof, that are liquid at room temperature, e.g. about 25° C., and about one atmosphere pressure.

Polymeric Compositions

Compositions comprising a polymer having branched silicone substituted by at least one alkylcarboxy group in a free or salt form and cross-linked with an alkyl functional cross-linker, wherein an average number of alkylcarboxy substitutions per silicone is between 1 and 60 and an average number of crosslinks between branched silicones being between 1 and 30 are described herein. In some aspects, the average number of alkylcarboxy substitutions per silicone is between 1 and 15. In some aspects, the average number of alkylcarboxy substitutions per silicone is between 1 and 12. In some aspects, the average number of alkylcarboxy substitutions per silicone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60.

In some aspects, the average number of crosslinks between branched silicones is between 1 and 15. In some aspects, the average number of crosslinks between branched silicones is between 1 and 12. In some aspects, the average number of crosslinks between branched silicones is 1, 2, 3, 4, 5, 6, 7, 8, 9, 10, 11, or 12.

In some aspects, the polymer is prepared by a method comprising
(a) reacting
 i. a Si—H functional compound of formula (I):

$$[SiO_{4/2}]_a[R^1SiO_{3/2}]_b[R^2MeSiO_{2/2}]_c[HMeSiO_{2/2}]_d[R^3Me_2SiO_{1/2}]_e[HMe_2SiO_{1/2}]_f \quad (I)$$

wherein
R$^1$ is hydrogen, an aliphatic, aromatic, or fluoro monovalent hydrocarbon having from 1 to 60 carbon atoms;
R$^2$ and R$^3$ are each an aliphatic, aromatic, or fluoro monovalent hydrocarbon having from 1 to 60 carbon atoms; and
a≥0, b≥0, a+b≥1, c≥0, d≥0, e≥0, f>1, and d+f≥2;
 ii. a carboxy functional olefin of formula (II):

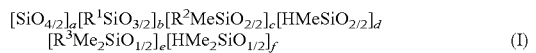

(II)

wherein
R' is hydrogen or —Si(R$^a$)$_3$ wherein R$^a$ is an aliphatic monovalent hydrocarbon;
n is 0≤n≤30 and
 iii. a silicone based alkenyl functional cross-linker of formula (III) and/or a non-silicone based alkenyl functional cross-linker of formula (IV):

$$M^1_{a'}M^2_{b'}D^1_{c'}D^2_{d'}T^1_{e'}T^2_{f'}Q_{g'}, \quad (III)$$

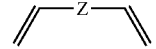 (IV)

wherein:
M$^1$=R$^4$R$^5$R$^6$SiO$_{1/2}$;
M$^2$=R$^7$R$^8$R$^9$SiO$_{1/2}$;
D$^1$=R$^{10}$R$^{11}$SiO$_{2/2}$;
D$^2$=R$^{12}$R$^{13}$SiO$_{2/2}$;
T$^1$=R$^{14}$SiO$_{3/2}$;
T$^2$=R$^{15}$SiO$_{3/2}$;
Q=SiO$_{4/2}$;
wherein
R$^5$, R$^6$, R$^7$, R$^8$, R$^9$, R$^{11}$, R$^{12}$, R$^{13}$, and R$^{15}$ are independently an aliphatic, aromatic, or fluoro monovalent hydrocarbon having from 1 to 60 carbon atoms;
R$^4$, R$^{10}$, and R$^{14}$ are each a monovalent radical containing at least one terminal olefin bond;
a', b', c', d', e', f' and g' are independently zero or a positive integer, such that 2≤a'+b'+c'+d'+e'+f'+g'≤6000 and when a'+c'+e'=2, d+f=2 or when d+f=2, a'+c'+e'>2; and
Z is an aliphatic hydrocarbon with 1 to 60 carbon atoms; and
(b) deprotecting the reaction product of step (a) to replace the —Si(R$^a$)$_3$ group with a hydrogen.

The polymer can be prepared by mixing the components in any order. Additionally, each component can be added simultaneously or sequentially, or as batch or semi-batch preparations.

The disclosure also relates to methods for preparing the polymer comprising reacting:
 i. a Si—H functional compound of formula (I):

$$[SiO_{4/2}]_a[R^1SiO_{3/2}]_b[R^2MeSiO_{2/2}]_c[HMeSiO_{2/2}]_d[R^3Me_2SiO_{1/2}]_e[HMe_2SiO_{1/2}]_f \quad (I)$$

wherein
R$^1$ is hydrogen or an aliphatic, aromatic, or fluoro monovalent hydrocarbon having from 1 to 60 carbon atoms;
R$^2$ and R$^3$ are each an aliphatic, aromatic, or fluoro monovalent hydrocarbon having from 1 to 60 carbon atoms; and
a≥0, b≥0, a+b≥1, c≥0, d≥0, e≥0, f>1, and d+f≥2;
 ii. a carboxy functional olefin of formula (II):

(II)

wherein
R' is hydrogen or —Si(R$^a$)$_3$ wherein R$^a$ is an aliphatic monovalent hydrocarbon;
n is 0≤n≤30; and
 iii. a silicone based alkenyl functional cross-linker of formula (III) and/or a non-silicone based alkenyl functional cross-linker of formula (IV):

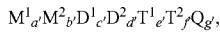
(III)

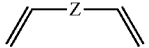
(IV)

wherein:
$M^1 = R^4R^5R^6SiO_{1/2}$;
$M^2 = R^7R^8R^9SiO_{1/2}$;
$D^1 = R^{10}R^{11}SiO_{2/2}$;
$D^2 = R^{12}R^{13}SiO_{2/2}$;
$T^1 = R^{14}SiO_{3/2}$;
$T^2 = R^{15}SiO_{3/2}$; and
$Q = SiO_{4/2}$;
wherein
$R^5$, $R^6$, $R^7$, $R^8$, $R^9$, $R^{11}$, $R^{12}$, $R^{13}$, and $R^{15}$ are independently an aliphatic, aromatic, or fluoro monovalent hydrocarbon having from 1 to 60 carbon atoms;
$R^4$, $R^{10}$, and $R^{14}$ are each a monovalent radical containing at least one terminal olefin bond;
a', b', c', d', e', f' and g' are independently zero or a positive integer, such that $2 \le a'+b'+c'+d'+e'+f'+g' \le 6000$ and when a'+c'+e'=2, d+f>2 or when d+f=2, a'+c'+e'>2; and
Z is an aliphatic hydrocarbon with 1 to 60 carbon atoms.

The polymer can be prepared by mixing the components in any order. Additionally, each component can be added simultaneously or sequentially, or as batch or semi-batch preparations.

The disclosure further relates to preparing a polymer comprising deprotecting a reaction product of
i. a Si—H functional compound of formula (I):

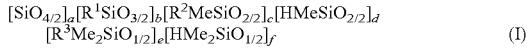

$$[SiO_{4/2}]_a[R^1SiO_{3/2}]_b[R^2MeSiO_{2/2}]_c[HMeSiO_{2/2}]_d[R^3Me_2SiO_{1/2}]_e[HMe_2SiO_{1/2}]_f \quad (I)$$

wherein
$R^1$ is hydrogen, an aliphatic, aromatic, or fluoro monovalent hydrocarbon having from 1 to 60 carbon atoms;
$R^2$ and $R^3$ are each an aliphatic, aromatic, or fluoro monovalent hydrocarbon having from 1 to 60 carbon atoms; and
$a \ge 0$, $b \ge 0$, $a+b \ge 1$, $c \ge 0$, $d \ge 0$, $e \ge 0$, $f > 1$, and $d+f \ge 2$;
ii. a carboxy functional olefin of formula (II):

(II)

wherein
R' is hydrogen or —Si(R$^a$)$_3$ wherein R$^a$ is an aliphatic monovalent hydrocarbon;
n is $0 \le n \le 30$; and
iii. a silicone based alkenyl functional cross-linker of formula (III) and/or a non-silicone based alkenyl functional cross-linker of formula (IV):

(III)

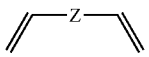
(IV)

wherein:
$M^1 = R^4R^5R^6SiO_{1/2}$;
$M^2 = R^7R^8R^9SiO_{1/2}$;
$D^1 = R^{10}R^{11}SiO_{2/2}$;
$D^2 = R^{12}R^{13}SiO_{2/2}$;
$T^1 = R^{14}SiO_{3/2}$;
$T^2 = R^{15}SiO_{3/2}$; and
$Q = SiO_{4/2}$;
wherein
$R^5$, $R^6$, $R^7$, $R^8$, $R^9$, $R^{11}$, $R^{12}$, $R^{13}$, and $R^{15}$ are independently an aliphatic, aromatic, or fluoro monovalent hydrocarbon having from 1 to 60 carbon atoms;
$R^4$, $R^{10}$, and $R^{14}$ are each a monovalent radical containing at least one terminal olefin bond;
a', b', c', d', e', f' and g' are independently zero or a positive integer, such that $2 \le a'+b'+c'+d'+e'+f'+g' \le 6000$ and when a'+c'+e'=2, d+f>2 or when d+f=2, a'+c'+e'>2; and
Z is an aliphatic hydrocarbon with 1 to 60 carbon atoms.

The polymer can be prepared by mixing the components in any order. Additionally, each component can be added simultaneously or sequentially, or as batch or semi-batch preparations.

In some aspects, the method further comprises deprotecting the reaction product to replace the —Si(R$^a$)$_3$ group with a hydrogen.

The reaction between the Si—H functional compound of formula (I), carboxy functional olefin of formula (II), and silicone based alkenyl functional cross-linker of formula (III) or non-silicone based alkenyl functional cross-linker of formula (IV) occurs in the presence of a suitable solvent. The suitable solvent can be a low viscosity silicone fluid or a volatile silicone fluid or organic solvents. Examples of suitable solvents include, but are not limited to isodecane, isohexadecane, squalane, hemisqualane, hydrogenated polyisobutene, jojoba, cylcopentasiloxane, dimethicone, bisphenylpropyl dimethicone, octyldodecyl neo-pentanoate, isopropyl myristate, isononyl isononanoate, oleyl oleate, oleyl alcohol, isomyristyl alcohol, or combinations thereof.

In some aspects, the reaction between the Si—H functional compound of formulation (I), the carboxy functional olefin of formula (II) and the alkenyl functional cross-linker of formula (III) and/or (IV) occurs in the presence of at least one precious metal catalyst selected from the group consisting of a rhodium, ruthenium, palladium, osmium, iridium, and platinum catalyst. In some aspects, at least one of the platinum catalysts is selected from the group consisting of (PtCl$_2$Olefin), H(PtCl$_3$Olefin), platinic chloride, chloroplatinic acid, bis(acetylacetonato)platinum, (η5-Cyclopentadienyl)trialkylplatinum, a cyclopropane complex of platinum chloride, and a complex formed from chloroplatinic acid.

In some aspects, the platinum containing material can be a complex formed from chloroplatinic acid with up to 2 moles per gram of platinum of a member selected from the class consisting of alcohols, ethers, aldehydes and mixtures of the above as described in U.S. Pat. No. 3,220,972 hereby incorporated by reference. The catalysts most specifically used herein are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in Advances in Organometallic Chemistry, volume 17, pages 407 through 447, F. G. A. Stone and R. West editors, published by the Academic Press (New York, 1979). In some aspects, the platinum catalyst is a soluble complex form.

The amount of precious metal catalyst utilized in the reaction can range from between about 0.1 and about 10,000 ppm. In some aspects, the amount of precious metal catalyst can range from between about 1 and about 1,000 ppm. In some aspects, the amount of precious metal catalyst can range from between about 1 and 500 ppm. In some aspects, the amount of precious metal catalyst can range from between about 1 and 250 ppm. In some aspects, the amount of precious metal catalyst can range from between about 1 and 100 ppm.

In some aspects, $R^1$ is an aliphatic, aromatic, or fluoro monovalent hydrocarbon. In some aspects, $R^1$ is a $C_1$-$C_{30}$ monovalent hydrocarbon. In some aspects, $R^1$ is a $C_1$-$C_{18}$ monovalent hydrocarbon. In some aspects, $R^1$ is a $C_1$-$C_{12}$ or $C_1$-$C_6$ monovalent hydrocarbon. In some aspects, $R^1$ is an aliphatic monovalent hydrocarbon. In some aspects, $R^1$ is an aromatic hydrocarbon. In some aspects, $R^1$ is a $C_6$-$C_{14}$ aromatic hydrocarbon. In some aspects, $R^1$ is phenyl.

In some aspects, one or more of $R^2$ and $R^3$ is a $C_1$-$C_{30}$ monovalent hydrocarbon. In some aspects, the one or more of $R^2$ and $R^3$ is a $C_1$-$C_{18}$ monovalent hydrocarbon.

In some aspects, $R^a$ is a $C_1$-$C_{12}$ group. In some aspects, $R^a$ is a $C_1$-$C_8$ group. In some aspects, $R^a$ is selected from the group consisting of methyl, ethyl, propyl, butyl, pentyl, hexyl, and heptyl. In some aspects, $R^a$ is methyl.

In some aspects, one or more of $R^5$, $R^6$, $R^7$, $R^8$, $R^9$, $R^{11}$, $R^{12}$, $R^{13}$, and $R^{15}$ is a $C_1$-$C_{30}$ monovalent hydrocarbon. In some aspects, the one or more of $R^5$, $R^6$, $R^7$, $R^8$, $R^9$, $R^{11}$, $R^{12}$, $R^{13}$, and $R^{15}$ is an aliphatic monovalent hydrocarbon. In some aspects, the one or more of $R^5$, $R^6$, $R^7$, $R^8$, $R^9$, $R^{11}$, $R^{12}$, $R^{13}$, and $R^{15}$ is selected from the group consisting of methyl, ethyl, n-propyl, isopropyl, n-butyl, isobutyl, tert-butyl, n-pentyl, isopentyl, neo-pentyl, tert-pentyl, hexyl, heptyl, octyl, nonyl, decyl, and cycloalkyl. In some aspects, the one or more of $R^5$, $R^6$, $R^7$, $R^8$, $R^9$, $R^{11}$, $R^{12}$, $R^{13}$, and $R^{15}$ is selected from the group consisting of n-hexyl, n-heptyl, n-octyl, isooctyl, 2,2,4-trimethylpentyl, n-nonyl, n-decyl, cyclopentyl, cyclohexyl, cycloheptyl, and methylcyclohexyl.

In some aspects, one or more of $R^5$, $R^6$, $R^7$, $R^8$, $R^9$, $R^{11}$, $R^{12}$, $R^{13}$, and $R^{15}$ is an aromatic monovalent hydrocarbon. In some aspects, the one or more of $R^5$, $R^6$, $R^7$, $R^8$, $R^9$, $R^{11}$, $R^{12}$, $R^{13}$, and $R^{15}$ is selected from the group consisting of phenyl, naphthyl, o-tolyl, m-tolyl, p-tolyl, xylyl, ethylphenyl, and benzyl.

In some aspects, one or more of $R^5$, $R^6$, $R^7$, $R^8$, $R^9$, $R^{11}$, $R^{12}$, $R^{13}$, and $R^{15}$ is a fluoro monovalent hydrocarbon. In some aspects, the one or more of $R^5$, $R^6$, $R^7$, $R^8$, $R^9$, $R^{11}$, $R^{12}$, $R^{13}$, and $R^{15}$ is a $C_1$-$C_{18}$ monovalent hydrocarbon.

In some aspects, a', b', c', d', e', f', and g' are $2 \leq a'+b'+c'+d'+e'+f'+g' \leq 4000$. In some aspects, a', b', c', d', e', f', and g' are $2 \leq a'+b'+c'+d'+e'+f'+g' \leq 2000$. In some aspects, a', c', and e' are $2 \leq a'+c'+e' \leq 120$. In some aspects, a', c', and e' are $2 \leq a'+c'+e' \leq 100$. In some aspects, a'=2, d'=75-600, and b'=c'=e'=f'=g'=0.

In some aspects, a=10, b=c=d=e=0, f=12, and n=8. In some aspects, a=0, b=1, c=d=e=0, f=3, and n=8.

In some aspects, Z is $-(CHR^{16})_m-$ or $-(CH_2CHR^{17}O)_k-$, wherein m and k are positive integers, such that $1 \leq m \leq 60$ and $1 \leq k \leq 500$, and $R^{16}$ and $R^{17}$ are independently hydrogen or monovalent hydrocarbon having from 1 to 60 carbon atoms. In some aspects, Z is $-(CHR^{16})_m-$, m is 1-30, and $R^{16}$ is from 1 to 30 carbon atoms. In some aspects, Z is $-(CHR^{16})_m-$, m is 1-18, and $R^{16}$ is from 1 to 20 carbon atoms. In some aspects, Z is $-(CH_2CHR^{17}O)_k-$, k is 1-250, and $R^{17}$ is from 1 to 30 carbon atoms. In some aspects, Z is $-(CH_2CHR^{17}O)_k-$, k is 1-100, and $R^{17}$ is from 1 to 20 carbon atoms.

In some aspects, the polymer is in a free form. In some aspects, the polymer is in a salt form. In some aspects, a cation of the salt form is independently selected from alkali metals, alkaline earth metals, transition metals, rare earth metals, metals, metal complexes, quaternary ammonium and phosphonium groups, organic cations, alkyl cations, cationic hydrocarbons, cationic polymers, or zwitterions.

The disclosure also relates to a product prepared by any of the methods described herein.

Personal Care Compositions

The disclosure additionally relates to personal care compositions comprising (a) a composition or product described herein; and (b) one or more personal care components. In one aspect, the personal care composition comprises a solvent.

In one aspect herein, the silicone compositions described herein are self-emulsifying. In another aspect, the personal care composition may be further processed under low to high shear to adjust the viscosity and sensory feel of the composition. This can be achieved, for example, by subjecting the composition to a moderate to high shearing force. High shear may be applied using, for example, a Sonolator apparatus, a Gaulin Homogenizer or a Micro Fluidizer apparatus. One or more carrier solvent may be added to the silicone composition prior to the shearing.

In one aspect, the personal care composition is a solid, typically having a creamy consistency, wherein the silicone polymer acts as a means for gelling the fluid to reversibly impart characteristics of a solid to the fluid. At rest, the personal care composition exhibits the properties of a solid gel material. The personal care composition can exhibit high stability and resistance to syneresis so that the personal care composition exhibits little or no tendency for fluid to flow from the personal care composition. The high stability and syneresis resistance persists with prolonged aging of the personal care compositions.

However, the solvent included in the personal care composition can be released from the polymers described herein by subjecting the personal care composition to a shearing force, such as, for example, by rubbing the composition between one's fingers, to provide improved sensory feel characteristic of the fluid component of the silicone material. Water (or a water equivalent such as a non-aqueous hydroxylic solvent), siloxane, linear or cyclic, or lipophilic fluid (oil swelling agent, oil swellable) can be used as the solvent which may function as a swelling agent. Lipophilic fluids suitable for use as the solvent component of the personal care composition are those described herein. In one aspect, the solvent component of the personal care composition exhibits a viscosity of below 1,000 cSt. In one aspect, the solvent component of the personal care composition exhibits a viscosity below 500 cSt. In one aspect, the solvent component of the personal care composition exhibits a viscosity of below 250 cSt. In one aspect, the solvent component of the personal care composition exhibits a viscosity of below 100 cSt, at 25° C.

In one aspect, the polymers described herein are soluble in various fluid components, and are capable of thickening the solvent. The amount of crosslinking present in the polymers described herein may be characterized with respect to the degree of thickening exhibited by the polymer in the solvent.

In another aspect, the cross linked structure of the polymers described herein is effective to allow the polymer to be swollen by a low molecular weight fluid, such as a silicone fluid, hydrophobic oil, or silicone and hydrocarbon fluid, such as, for example, decamethylcyclopentasiloxane, from its original volume to a swollen volume.

The polymers described herein can be utilized as prepared or as the hydrophobic component in a personal care composition that is an emulsion. Emulsions comprise at least two immiscible phases. One immiscible phase is continuous and the other is discontinuous. In one aspect, the non-miscible phase (immiscible phase) is aqueous, non-aqueous, or solid particulates.

Emulsions can be liquids with varying viscosities or solids. The particle size of the emulsions can make them microemulsions. When sufficiently small, the microemulsions can be transparent. It is also possible to prepare emulsions of emulsions which are generally known as multiple emulsions.

Examples of suitable emulsions for personal care compositions include: 1) aqueous emulsions where the discontinuous phase comprises water and the continuous phase comprises a polymer composition or product described herein; 2) aqueous emulsions where the discontinuous phase comprises a polymer composition or product described herein and the continuous phase comprises water; 3) non-aqueous emulsions where the discontinuous phase comprises a non-aqueous hydroxylic solvent and the continuous phase comprises a polymer composition or product described herein; and 4) non-aqueous emulsions where the continuous phase comprises a non-aqueous hydroxylic organic solvent and the discontinuous phase comprises a polymer composition or product described herein.

Examples of suitable non-aqueous hydroxylic organic solvents in the emulsions containing a polymer composition or product described herein include, but are not limited to, ethylene glycol, ethanol, propyl alcohol, isopropyl alcohol, propylene glycol, dipropylene glycol, tripropylene glycol, butylene glycol, isobutylene glycol, methyl propane diol, glycerin, sorbitol, polyethylene glycol, polypropylene glycol mono alkyl ethers, polyoxyalkylene copolymers and mixtures thereof.

In one aspect, the polymers described herein are compatible with a particulate additive. In one aspect, the particulate additive is an inorganic particulate, polymeric latex, and/or a pigment. In another aspect, the polymers are capable of suspending these particles for a prolonged period in personal care formulations.

Once the desired emulsion is prepared, the resulting material is usually a high viscosity cream with good feel characteristics and high absorbance of volatile solvents. The emulsion can then be blended into personal care compositions for hair care, skin care, and the like.

The personal care composition can be a personal care application including deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products (e.g., nail polish, nail polish remover, nail creams and lotions, cuticle softeners), protective creams (e.g., sunscreen, insect repellent and anti-aging products), color cosmetics (e.g., lipsticks, foundations, face powders, eye liners, eye shadows, blushes, makeup, and mascaras). The personal care application can also be a drug delivery system for topical application of a medicinal composition that can be applied to the skin.

In one aspect, the personal care composition further comprises one or more personal care ingredients. Suitable personal care ingredients include, for example, emollients, moisturizers, humectants, pigments (e.g., pearlescent pigments such as bismuth oxychloride and titanium dioxide coated mica), colorants, fragrances, biocides, preservatives, antioxidants, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents (e.g., fumed silica or hydrated silica), particulate fillers (e.g., talc, kaolin, starch, modified starch, mica, nylon, clays, such as, for example, bentonite and organo-modified clays).

In some aspects, the one or more personal care components included in the personal care compositions are selected from the group consisting of a humectant, emollient, moisturizer, pigment, colorant, fragrance, biocide, preservative, antioxidant, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, and thickening agent. In some aspects, the one or more emollients is selected from the group consisting of triglyceride esters, wax esters, alkyl or alkenyl ester of fatty acids, polyhydric alcohol esters, and mixtures thereof. In some aspects, the one or more personal care components is a silicone oil, an organic oil, or mixtures thereof.

In one aspect, the personal care composition is an antiperspirant composition that comprises a polymer composition or product described herein and one or more active antiperspirant agents. Suitable antiperspirant agents include, but are not limited to, the Category I active antiperspirant ingredients listed in the U.S. Food and Drug Administration's Oct. 10, 1993 Monograph on antiperspirant drug products for over-the-counter human use including aluminum halides, aluminum hydroxyhalides, for example, aluminum chlorohydrate, and complexes or mixtures thereof with zirconyl oxyhalides and zirconyl hydroxyhalides, (e.g., aluminum-zirconium chlorohydrate, and aluminum zirconium glycine complexes, such as aluminum zirconium tetrachlorohydrex gly).

In another aspect, the personal care composition is a skin care composition comprising a polymer composition or product described herein, and a vehicle, such as a silicone oil or an organic oil. The skin care composition can also include emollients, such as triglyceride esters, wax esters, alkyl or alkenyl esters of fatty acids or polyhydric alcohol esters, pigments, vitamins (e.g., Vitamin A, Vitamin C and Vitamin E), sunscreen or sunblock compounds (e.g., titanium dioxide, zinc oxide, oxybenzone, octylmethoxy cinnamate, butylmethoxy dibenzoylm ethane, p-aminobenzoic acid and octyl dimethyl-p-aminobenzoic acid).

In yet another aspect, the personal care composition is a color cosmetic composition such as a lipstick, a makeup or mascara. The color cosmetic composition comprises a polymer composition or product described herein and a coloring agent (e.g., pigment, water-soluble dye, or liposoluble dye).

In still yet another aspect, the personal care composition comprises a polymer composition or product described herein and fragrant materials. The fragrant materials can be fragrant compounds, encapsulated fragrant compounds or fragrance releasing compounds that either the neat compounds or are encapsulated.

EXAMPLES

The following synthetic (1-19) and formulation examples (F1-F7 and 1-12) are illustrative, but not limiting, of the methods described herein. Other suitable modifications and adaptations of the variety of conditions and parameters normally encountered in the field, and which are obvious to those skilled in the art, are within the spirit and scope of the invention.

Synthetic Example 1

Hemisqualane (94.38 g), a poly(dimethylhydrosiloxy)silicate (8.86 g, 79.74 mmol) and silyl undecylenic acid ester (23.94 g, 95.5 mmol) were added into a reactor. To this mixture, platinum(0)-1,3-divinyl-1,1,3,3-tetramethyldisiloxane complex (0.002 g Pt) dissolved in hemisqualane (5 mL) was added. The reactor was closed and the air inside was replaced by flashing with nitrogen. The mixture was continued to slowly shear mix at room temperature for an hour to facilitate the hydrosilylation of poly(dimethylhydrosiloxy)silicate with the undecylenic acid ester. A vinyl terminal polydimethylsiloxane (45.85 g, 7.97 mmol) dissolved in hemisqualane (23.60 g) and platinum(0)-1,3-divinyl-1,1,3,3-tetramethyldisiloxane complex (0.002 g Pt) were added. The reaction temperature was raised to 85° C. and allowed to shear the mixture for additional 3 hours when the entire reaction mixture was transformed into a viscous gel. To this, deionized water (3.37 g) was added, and continued to stir at 85° C. for an hour. Then the reaction mixture was vacuum stripped at 85° C. and 150 mmHg for 30 minutes when the product was obtained as a transparent gel.

Synthetic Example 2

Hemisqualane (238.5 g), a poly(dimethylhydrosiloxy)silicate (8.23g, 74.07 mmol) and silyl undecylenic acid ester (22.22 g, 86.63 mmol) were added into a reactor. To this mixture, platinum(0)-1,3-divinyl-1,1,3,3-tetramethyldisiloxane complex (0.005 g Pt) dissolved in hemisqualane (5 mL) was added. The reactor was closed and the air inside was replaced by flashing with nitrogen. The mixture was continued to slowly shear mix at room temperature for an hour to facilitate the hydrosilylation of poly(dimethylhydrosiloxy)silicate with the undecylenic acid ester. A vinyl terminal polydimethylsiloxane (168.3 g, 7.4 mmol) dissolved in hemisqualane (59.62 g) and platinum(0)-1,3-divinyl-1,1,3,3-tetramethyldisiloxane complex (0.005 g Pt) were added. The reaction temperature was raised to 85° C. and allowed to shear the mixture for additional 3 hours when the entire reaction mixture was transformed into a viscous gel. To this, deionized water (3.12 g, 173.0 mmol) was added, and continued to stir at 85° C. for an hour. Then the reaction mixture was vacuum stripped at 85° C. and 150 mmHg for 30 minutes when the product was obtained as a transparent gel.

Synthetic Example 3

A poly(dimethylhydrosiloxy)silicate (4.13 g, 37.17 mmol), silyl undecylenic acid ester (11.11 g, 43.31 mmol) and isopropyl myristate (119.25 g) were added into a reactor. To this mixture, platinum(0)-1,3-divinyl-1,1,3,3-tetramethyl di siloxane complex (0.0025 g Pt) dissolved in isopropyl myristate (5 mL) was added. The reactor was closed and the air inside was replaced by flashing with nitrogen. The mixture was continued to slowly shear mixed at room temperature for an hour to facilitate the hydrosilylation of poly(dimethylhydrosiloxy)silicate with the undecylenic acid ester. A vinyl terminal polydimethylsiloxane (84.13 g, 3.7 mmol) dissolved in isopropyl myristate (29.81 g) and platinum(0)-1,3-divinyl-1,1,3,3-tetramethyldisiloxane complex (0.0025 g Pt) were added. The reaction temperature was raised to 85° C., and allowed to shear the mixture for additional 3 hours when the entire reaction mixture was transformed into a viscous gel. To this, deionized water (1.56 g, 86.5 mmol) was added, and continued to stir at 85° C. for an hour. Then the reaction mixture was vacuum stripped at 85° C. and 150 mmHg for 30 minutes when the product was obtained as a soft gel.

Synthetic Example 4

A poly(dimethylhydrosiloxy)silicate (4.13 g, 37.17 mmol), silyl undecylenic acid ester (11.11 g, 43.31 mmol) and isononyl isononanoate (119.25 g) were added into a reactor. To this mixture, platinum(0)-1,3-divinyl-1,1,3,3-tetramethyldisiloxane complex (0.0025 g Pt) dissolved in isononyl isononanoate (5 mL) was added. The reactor was closed and the air inside was replaced by flashing with nitrogen. The mixture was continued to slowly shear mixed at room temperature for an hour to facilitate the hydrosilylation of poly(dimethylhydrosiloxy)silicate with the undecylenic acid ester. A vinyl terminal polydimethylsiloxane (84.13 g, 3.7 mmol) dissolved in isononyl isononanoate (29.81 g) and platinum(0)-1,3-divinyl-1,1,3,3-tetramethyldisiloxane complex (0.0025 g Pt) were added. The reaction temperature was raised to 85° C. and allowed to shear the mixture for additional 3 hours when the entire reaction mixture was transformed into a viscous gel. To this, deionized water (1.56 g, 86.5 mmol) was added, and continued to stir at 85° C. for an hour. Then the reaction mixture was vacuum stripped at 85° C. and 150 mmHg for 30 minutes when the product was obtained as a soft gel.

Synthetic Example 5

Tris(dimethylsiloxy)phenylsilane (1.3 g, 11.8 mmol), silyl undecylenic acid ester (1.07 g, 4.17 mmol) and hemisqualane (223.19 g) were added into a reactor. To this mixture, platinum(0)-1,3-divinyl-1,1,3,3-tetramethyldisiloxane complex (0.0037 g Pt) dissolved in hemisqualane (5 mL) was added. The reactor was closed and the air inside was replaced by flashing with nitrogen. The mixture was continued to slowly shear mixed at room temperature for an hour to facilitate the hydrosilylation of poly(dimethylhydrosiloxy)silicate with the undecylenic acid ester. A vinyl terminal polydimethylsiloxane (88.4 g, 3.88 mmol) dissolved in element 14 PDMS 350 cst fluid (55.80 g) and platinum(0)-1,3-divinyl-1,1,3,3-tetramethyldisiloxane complex (0.0037 g Pt) were added. The reaction temperature was raised to 85° C. and allowed to shear the mixture for additional 3 hours when the entire reaction mixture was transformed into a viscous gum. To this, deionized water (1.56 g, 86.5 mmol) was added, and continued to stir at 85° C. for an hour. Then the reaction mixture was vacuum stripped at 85° C. and 150 mmHg for 30 minutes when the product was obtained as a viscous gum.

Synthetic Example 6

A poly(dimethylhydrosiloxy)silicate (0.97 g, 8.73 mmol), silyl undecylenic acid ester (2.29 g, 8.92 mmol), a vinyl terminal polydimethylsiloxane (21.23 g, 2.78 mmol), element 14 PDMS 350 cst fluid (15.04 g), hemisqualane (60.15 g) and platinum(0)-1,3-divinyl-1,1,3,3-tetramethyldisiloxane complex (0.001 g Pt) were added into a reactor. The reactor was closed and the air inside was replaced by flashing with nitrogen. Then the mixture was shear mixed at room temperature for an hour and at 85° C. for 3 hours when the entire reaction mixture was transformed into a rubbery gel, and then additional amount of hemisqualane (66.48 g) was added, and continued stirring for an hour. To this, deionized water (0.30 g, 17.2 mmol) was added, and continued to stir at 85° C. for an hour. Then the reaction mixture was vacuum stripped at 85° C. and 150 mmHg for 30 minutes when the product was obtained as a soft gel.

Synthetic Example 7

A poly(dimethylhydrosiloxy)silicate (0.99 g, 8.91 mmol), silyl undecylenic acid ester (1.94 g, 7.55 mmol), a vinyl terminal polydimethylsiloxane (21.57 g, 2.82 mmol), element 14 PDMS 350 cst fluid (15.04 g), hemisqualane (60.15 g) and platinum(0)-1,3-divinyl-1,1,3,3-tetramethyldisiloxane complex (0.001 g, 10 ppm Pt) were added into a reactor. The reactor was closed and the air inside was replaced by flashing with nitrogen. Then the mixture was stirred shear mixed at room temperature for an hour and at 85° C. for 3 hours when the entire reaction mixture was transformed into a rubbery gel, and then additional amount of hemisqualane (66.48 g) was added, and continued stirring for an hour. To this, deionized water (0.30 g, 17.2 mmol) was added, and continued to stir at 85° C. for an hour. Then the reaction mixture was vacuum stripped at 85° C. and 150 mmHg for 30 minutes when the product was obtained as a soft gel.

Synthetic Example 8

A poly(dimethylhydrosiloxy)silicate (1.26 g, 11.34 mmol), silyl undecylenic acid ester (2.48 g, 9.67 mmol), a vinyl terminal polydimethylsiloxane (20.74 g, 3.66 mmol), element 14 PDMS 350 cst fluid (15.03 g), hemisqualane (60.14 g) and platinum(0)-1,3-divinyl-1,1,3,3-tetramethyldisiloxane complex (0.001 g Pt) were added into a reactor. The reactor was closed and the air inside was replaced by flashing with nitrogen. Then the mixture was shear mixed at room temperature for an hour and at 85° C. for 3 hours when the entire reaction mixture was transformed into a rubbery gel, and then additional amount of hemisqualane (66.48 g) was added, and continued stirring for an hour. To this, deionized water (0.30 g, 17.2 mmol) was added, and continued to stir at 85° C. for an hour. Then the reaction mixture was vacuum stripped at 85° C. and 150 mmHg for 30 minutes when the product was obtained as a soft gel.

Synthetic Example 9

A poly(dimethylhydrosiloxy)silicate (1.23 g, 11.07 mmol), silyl undecylenic acid ester (2.91 g, 11.6 mmol), a vinyl terminal polydimethylsiloxane (20.32 g, 3.53 mmol), element 14 PDMS 350 cst fluid (15.03 g), hemisqualane (60.14 g) and platinum(0)-1,3-divinyl-1,1,3,3-tetramethyldisiloxane complex (0.001 g Pt) were added into a reactor. The reactor was closed and the air inside was replaced by flashing with nitrogen. Then the mixture was stirred under shear at room temperature for an hour and at 85° C. for 3 hours when the entire reaction mixture was transformed into a rubbery gel. Added additional amount of hemisqualane (66.48 g) and continued stirring for an hour. To this, deionized water (0.30 g) was added, and continued to stir at 85° C. for an hour. The reaction mixture was vacuum stripped at 85° C. and 150 mmHg for 30 minutes when the product was obtained as a clear transparent gel.

Synthetic Example 10

A poly(dimethylhydrosiloxy)silicate (9.87 g, 88.83 mmol), silyl undecylenic acid ester (23.29 g, 92.92 mmol), a vinyl terminal polydimethylsiloxane (162.56 g, 28.28 mmol), element 14 PDMS 350 cst fluid (120.0 g), hemisqualane (480.8 g) and platinum(0)-1,3-divinyl-1,1,3,3-tetramethyldisiloxane complex (0.008 g Pt) were added into a reactor. The reactor was closed and the air inside was replaced by flashing with nitrogen. The mixture was stirred under shear at room temperature for an hour and at 85° C. for 3 hours when the entire reaction mixture was transformed into a rubbery gel. Added an additional amount of hemisqualane (69.28 g) and continued stirring for an hour. To this, deionized water (3.27 g) was added, and continued to stir at 85° C. for an hour. The reaction mixture was vacuum stripped at 85° C. and 150 mmHg for 30 minutes when the product was obtained as a translucent gel.

Synthetic Example 11

A poly(dimethylhydrosiloxy)silicate (3.70 g, 33.3 mmol), silyl undecylenic acid ester (8.73 g, 34.83 mmol), a vinyl terminal polydimethylsiloxane (60.96 g, 10.60 mmol), element 14 PDMS 350 cst fluid (45.07 g), hemisqualane (180.3 g) and platinum(0)-1,3-divinyl-1,1,3,3-tetramethyldisiloxane complex (0.003 g Pt) were added into a reactor. The reactor was closed and the air inside was replaced by flashing with nitrogen. The mixture was stirred under shear at room temperature for an hour and at 85° C. for 3 hours when the entire reaction mixture was transformed into a rubbery gel. Added an additional amount of hemisqualane (74.69 g) and continued stirring for an hour. To this, deionized water (3.27 g) was added, and continued to stir at 85° C. for an hour. The reaction mixture was vacuum stripped at 85° C. and 150 mmHg for 30 minutes when the product was obtained as a transparent gel.

Synthetic Example 12

A poly(dimethylhydrosiloxy)silicate (1.33 g, 11.97 mmol), silyl undecylenic acid ester (3.13 g, 12.48 mmol), a vinyl terminal polydimethylsiloxane (86.33 g, 4.14 mmol), element 14 PDMS 350 cst fluid (55.75 g), hemisqualane (223.02 g) and platinum(0)-1,3-divinyl-1,1,3,3-tetramethyldisiloxane complex (0.0037 g Pt) were added into a reactor. The reactor was closed and the air inside was replaced by flashing with nitrogen. The mixture was stirred under shear at room temperature for an hour and at 85° C. for 3 hours when the entire reaction mixture was transformed into a rubbery gel. Added an additional amount of hemisqualane (246.37 g), and continued stirring for an hour. To this, deionized water (3.27 g) was added, and continued to stir at 85° C. for an hour. The reaction mixture was vacuum stripped at 85° C. and 150 mmHg for 30 minutes when the product was obtained as a transparent gel.

Synthetic Example 13

A poly(dimethylhydrosiloxy)silicate (2.15 g, 19.35 mmol), silyl undecylenic acid ester (5.81 g, 23.18 mmol), a vinyl terminal polydimethylsiloxane (71.72 g, 1.93 mmol), element 14 PDMS 350 cst fluid (23.90 g), hemisqualane (95.61 g) and platinum(0)-1,3-divinyl-1,1,3,3-tetramethyldisiloxane complex (0.002 g Pt) were added into a reactor. The reactor was closed and the air inside was replaced by flashing with nitrogen. The mixture was stirred under shear at room temperature for an hour and at 85° C. for 3 hours when the entire reaction mixture was transformed into a rubbery gel. To this, deionized water (0.82 g) was added, and continued to stir at 85° C. for an hour. The reaction mixture was vacuum stripped at 85° C. and 150 mmHg for 30 minutes when the product was obtained as a viscous gel.

Synthetic Example 14

A poly(dimethylhydrosiloxy)silicate (0.72 g, 6.48 mmol), silyl undecylenic acid ester (1.14 g, 4.44 mmol), a vinyl terminal polydimethylsiloxane (47.23 g, 2.26 mmol), element 14 PDMS 350 cst fluid (30.15 g), hemisqualane (120.6 g) and platinum(0)-1,3-divinyl-1,1,3,3-tetramethyldisiloxane complex (0.002 g Pt) were added into a reactor. The reactor was closed and the air inside was replaced by flashing with nitrogen. The mixture was stirred under shear at room temperature for an hour and at 85° C. for 3 hours when the entire reaction mixture was transformed into a rubbery gel. Added additional amount of hemisqualane (133.5 g) and stirred for an hour. To this mixture, deionized water (0.21 g) was added, and continued to stir at 85° C. for an hour. The reaction mixture was vacuum stripped at 85° C. and 150 mmHg for 30 minutes when the product was obtained as a transparent gel.

Synthetic Example 15

Hemisqualane (481.80 g), poly(dimethylhydrosiloxy)silicate (11.90 g, 107.1 mmol) and silyl undecylenic acid ester (20.00 g, 77.8 mmol), a vinyl terminal polydimethylsiloxane (42.90 g, 7.46 mmol), element 14 PDMS 350 cst fluid (120.40 g), platinum(0)-1,3-divinyl-1,1,3,3-tetramethyldisiloxane complex (0.01 g Pt) were added into a reactor. The reactor was closed and the air inside was replaced by flashing with nitrogen. The mixture was stirred under shear at 85° C. for an hour. To this reaction mixture was added additional amount of vinyl terminal polydimethylsiloxane (120 g, 20.88 mmol) and platinum(0)-1,3-divinyl-1,1,3,3-tetramethyldisiloxane complex (0.01 g Pt), and continued to stir under shear for 3 hours when the entire reaction mixture was transformed into a rubbery gel. Added an additional amount of hemisqualane (199.5 g) and stirred for another hour. To this mixture, deionized water (13.2 g, 733 mmol) was added, and continued to stir at 85° C. for an hour. The reaction mixture was vacuum stripped at 85° C. and 150 mmHg for 30 minutes when the product was obtained as a transparent gel.

Synthetic Example 16

A poly(dimethylhydrosiloxy)silicate (2.15 g, 19.35 mmol), silyl undecylenic acid ester (5.81 g, 23.18 mmol), bis methallyl terminal poly(ethylene glycol-co-propylene glycol) with about 60% E0 and 40% PO (2.00 g, 1.32 mmol), a vinyl terminal polydimethylsiloxane (14.34 g, 0.386 mmol), element 14 PDMS 350 cst fluid (23.90 g), hemisqualane (95.61 g) and platinum(0)-1,3-divinyl-1,1,3,3-tetramethyldisiloxane complex (0.002 g Pt) were added into a reactor. The reactor was closed and the air inside was replaced by flashing with nitrogen. The mixture was stirred under shear at room temperature for an hour and at 85° C. for 3 hours when the entire reaction mixture was transformed into a rubbery gel. To this mixture, deionized water (0.82 g) was added, and continued to stir at 85° C. for an hour. The reaction mixture was vacuum stripped at 85° C. and 150 mmHg for 30 minutes when the product was obtained as a milky white gel.

Synthetic Example 17

A poly(dimethylhydrosiloxy)silicate (7.13 g, 64.17 mmol), silyl undecylenic acid ester (6.30 g, 24.61 mmol), undecylenic acid (3.57 g, 19.40 mmol), a vinyl terminal polydimethylsiloxane (25.74 g, 4.47 mmol), element 14 PDMS 350 cst fluid (72.24 g), hemisqualane (289.08 g) and platinum(0)-1,3-divinyl-1,1,3,3-tetramethyldisiloxane complex (0.008 g Pt) were added into a reactor. The reactor was closed and the air inside was replaced by flashing with nitrogen. The mixture was stirred under shear at 85° C. for an hour. Added an additional amount vinyl terminal polydimethylsiloxane (72.0 g, 12.52 mmol) and stirred at 85° C. for 3 hours when the entire reaction mixture was transformed into a soft gel. An additional amount of hemisqualane (119.7g) was added and stirred for an hour. To this mixture, deionized water (7.92 g) was added, and continued to stir at 85° C. for an hour. The reaction mixture was vacuum stripped at 85° C. and 150 mmHg for 30 minutes when the product was obtained as a clear gel.

Synthetic Example 18

A poly(dimethylhydrosiloxy)silicate (7.13 g, 64.17 mmol), silyl undecylenic acid ester (6.30 g, 24.61 mmol), allyloxy(polyethyleneoxide) (10.67 g, 19.40 mmol), a vinyl terminal polydimethylsiloxane (25.74 g, 4.47 mmol), element 14 PDMS 350 cst fluid (72.24 g), hemisqualane (289.08 g) and platinum(0)-1,3-divinyl-1,1,3,3-tetramethyldisiloxane complex (0.008 g Pt) were added into a reactor. The reactor was closed and the air inside was replaced by flashing with nitrogen. Then the mixture was stirred under shear at 85° C. for an hour. Added an additional amount of vinyl terminal polydimethylsiloxane (72.0 g, 12.52 mmol) and stirred at 85° C. for 3 hours when the entire reaction mixture was transformed into a soft gel. Additional amount of hemisqualane (119.7 g) was added and stirred for 1 hour. To this, deionized water (7.92 g) was added, and continued to stir at 85° C. for an hour. Then the reaction mixture was vacuum stripped at 85° C. and 150 mmHg for 30 minutes when the product was obtained as a translucent gel.

Synthetic Example 19

Hemisqualane (481.80 g), a poly(dimethylhydrosiloxy) silicate (11.88 g, 106.92 mmol), silyl undecylenic acid ester (19.23 g, 74.80 mmol), a vinyl terminal polydimethylsiloxane (42.90 g, 7.46 mmol), element 14 PDMS 350 cst fluid (120.40 g), and platinum(0)-1,3-divinyl-1,1,3,3-tetramethyldisiloxane complex (0.001 g Pt) were added into a reactor. The reactor was closed and the air inside was replaced by flashing with nitrogen. Then the mixture was stirred under shear at 85° C. for an hour. Added an additional amount vinyl terminal polydimethylsiloxane (120.00 g, 20.88 mmol), poly(dimethylhydrosiloxy)silicate (1.99 g, 17.97 mmol) and platinum(0)-1,3-divinyl-1,1,3,3-tetramethyldisiloxane complex (0.001 g Pt). The resulting mixture was continued to stir under shear at 85° C. for 2 hours when the entire reaction mixture was transformed into a gel powder. Additional amount of hemisqualane (199.50 g) was added and stirred for 1 hour. To this, deionized water (13.20 g, 733 mmol) was added, and continued to stir at 85° C. for an hour. Then the reaction mixture was vacuum stripped at 85° C. and 5 mmHg for 2 hours when the product was obtained as soft gel powder. The gel obtained was cooled and subjected to high shear homogenization using a rotor-stator homogenizer.

Comparative Example 1

Hemisqualane (90.45 g), a polymethylhydrosiloxane-co-polydimethylsiloxane (1.24 g, 4.91 mmol) and silyl undecylenic acid ester (0.86 g, 3.43 mmol) were added into a reactor. To this mixture, platinum(0)-1,3-divinyl-1,1,3,3-tetramethyldisiloxane complex (0.0015 g Pt) dissolved in hemisqualane (5 mL) was added. The reactor was closed and the air inside was replaced by flashing with nitrogen. The mixture was slowly shear mixed at room temperature for an hour to facilitate the hydrosilylation of polymethylhydrosiloxane with the undecylenic acid ester. A vinyl terminal polydimethylsiloxane (34.72 g, 1.66 mmol) dissolved in element 14 PDMS 350 cst oil (22.61 g) and platinum(0)-1,3-divinyl-1,1,3,3-tetramethyldisiloxane complex (0.0015 g Pt) were added. The reaction temperature was raised to 85° C. and allowed to shear the mixture for additional 3 hours when the entire reaction mixture was transformed into a viscous gel. Added an additional amount of hemisqualane (100 g) and stirred for an hour. To this mixture, deionized water (0.12 g) was added, and continued to stir at 85° C. for an hour. The reaction mixture was vacuum stripped at 85° C. and 150 mmHg for 30 minutes when the product was obtained as a transparent gel.

Comparative Example 2

A commercially available traditional silicone gel containing 5 wt % active network were used as one of the benchmarks.

It is evident from the Table 1 (CF1-CF2 and F1), the carboxy modified silicone gel has better water compatibility against comparative examples 1 and 2. Also, superior structuring performances of the carboxy modified silicone gels is evident by the higher viscosity of their blend with PDMS-5 cst in example F2-F7 compared to comparative example (CF2).

Formulation Example 1

Skin nourishing cream.

Procedure:
- Phase A & Phase B ingredients were weighed separately,
- Both phases were heated separately to 75-80° C.,
- Once temperature of both phases attained to 75-80° C., Phase B was added to Phase A under homogenization and mixed well,
- In a separate vessel, Phase C was prepared by mixing a carboxy modified silicone gel (Synthetic Example 14) and the remaining ingredients of the Phase C,
- Slowly cooled the mixture of Phase A and B between 60 to 50° C., and added Phase C ingredients and mixed until uniform,
- Poured product into suitable container.

TABLE 2

| Phase | Ingredients | International Nomenclature of Cosmetic Ingredients (INCI) | Supplier | % w/w |
|---|---|---|---|---|
| A | Water | Aqua | | 82.10 |
| | Glycerine | Glycerine | Sigma Aldrich | 3.00 |
| B | Brij™ S721 | Steareth-21 | Croda | 1.00 |
| | Brij™ S2 | Steareth-2 | Croda | 0.50 |
| | Crodamol GTCC | Caprylic/Capric Triglycerides | Croda | 3.00 |
| | Galaxy 610 | Ethylene Glycol Distearate | Galaxy Surfactant | 1.00 |
| | Cutina GMS V | Glyceryl Monostearate SE | BASF | 2.00 |
| | Ginol 16 (95%) | Cetyl Alcohol | Godrej | 1.00 |
| C | Synthetic Example 14 | | | 1.60 |
| | Element 14 PDMS 5 cst | Dimethicone | Momentive | 3.40 |

TABLE 1

Comparative compatibility and structuring performance data

| Ingredients | Network Content (%) | COOH Content (mmol/g) | CF1 | CF2 | CF3 | F1 | F2 | F3 | F4 | F5 | F6 | F7 |
|---|---|---|---|---|---|---|---|---|---|---|---|---|
| Synthetic Example 1 | 40 | 0.477 | | | | | | 10 | | | | |
| Synthetic Example 2 | 40 | 0.177 | | | | | | | 10 | 10 | | |
| Synthetic Example 9 | 15 | 0.071 | | | | | | | | | 10 | 10 |
| Synthetic Example 14 | 15 | 0.014 | | | | 23.5 | 10 | | | | | |
| Comparative Example 1 | 15 | 0.014 | | 23.5 | 10 | | | | | | | |
| Comparative Example 2 | 5 | — | 70.5 | | | | | | | | | |
| Deionized water | | | 36.8 | 41.2 | | 41.2 | | | | | | |
| PDMS-5 cst oil | | | | 35.3 | 90 | 35.3 | 90 | 90 | 89.9 | | 89.1 | |
| Isododecane | | | | | | | | | | 89.9 | | |
| Isopropyl Myristate | | | | | | | | | | | | 90 |
| Aqueous KOH (10 wt %) | | | | | | | | | 0.1 | 0.1 | 0.1 | |
| Total | | | 100 | 100 | 100 | 100 | 100 | 100 | 100 | 100 | 100 | 100 |
| Compatibility | | | No | No | Yes | Yes | Yes | Yes | Yes | Yes | Yes | Yes |
| Viscosity, Pas | | | — | — | 0.4 | — | 0.8 | — | 10.3 | — | 4.0 | 1.2 |

TABLE 2-continued

| Phase | Ingredients | International Nomenclature of Cosmetic Ingredients (INCI) | Supplier | % w/w |
|---|---|---|---|---|
| | Sepigel305 | Polyacrylamide (and) C13-14 Isoparaffin (and) Laureth | SEPPIC | 0.50 |
| | Euxyl ® PE 9010 | Phenoxyethanol (and) Ethylhexylglycerine | Schulke and Mayr | 0.70 |
| | Fragrance | Fragrance | Goldfield Fragrance Pvt. Ltd. | 0.20 |
| | | | Total | 100.00 |

Formulation Example 2

Facial cleanser.
Procedure:
 The ingredient of phases A, B, and C were mixed separately,
 Phase B was added to Phase A, and stirred gently,
 Phase C was added to the combined Phases of A and B,
 Once the mixture became homogeneous, poured product into suitable container.

TABLE 3

| Phase | Ingredients | INCI | Supplier | % w/w |
|---|---|---|---|---|
| A | Almond oil | Prunus Amygdalus Dulcis (Sweet Almond) Oil | | 2.00 |
| | Synthetic Example 14 Element 14-5 | Dimethicone -5 cst | Momentive | 5.00 7.00 |
| B | Sodium lauryl sulfate | Sodium lauryl sulfate | | 37.00 |
| | Cocamidopropyl betaine | Cocamidopropyl betaine | Galaxy Surfactants | 5.00 |
| | Glycerine | Glycerine | Sigma Aldrich | 1.00 |
| | Water | Aqua | | 39.60 |
| | Xanthan Gum | Xanthan Gum | Sigma Aldrich | 0.70 |
| C | D-Panthenol | D-Panthenol | DSM | 0.10 |
| | Tocopherol | Tocopherol | DSM | 0.10 |
| | Sodium Hydroxide | Sodium Hydroxide | Sigma Aldrich | 0.20 |
| | Preservation | Phenoxyethanol (and) Ethylhexylglycerin | Schulke & Mayr | 0.50 |
| | | | Total | 100.00 |

Formulation Example 3

Eye cream.
Procedure:
 Phase A and Phase B ingredients were mixed separately,
 Both phases were heated separately to 75-80° C.,
 Once temperature of both phases were attained to 75-80° C., added Phase B to Phase A under homogenization, and mixed well,
 In a separate vessel, Phase C was prepared by mixing a carboxy modified silicone gel (synthetic example 15) and the remaining ingredients of the Phase C,
 Slowly cooled the mixture of Phase A and B between 60 to 50° C., and added Phase C ingredients, and mixed until uniform,
 Once the batch became homogeneous, poured product into suitable container.

TABLE 4

| Phase | Ingredients | INCI | Supplier | % w/w |
|---|---|---|---|---|
| A | Water | Water | | 80.60 |
| | Glycerine | Glycerine | Sigma Aldrich | 3.00 |
| | Niacinamide | Niacinamide | Sigma Aldrich | 2.00 |
| | Brij ™ S721 | Steareth-21 | Croda | 1.00 |
| B | Brij ™ S2 | Steareth-2 | Croda | 0.50 |
| | Crodamol GTCC | Caprylic/Capric triglycerides | Croda | 3.00 |
| | Galaxy 610 | Ethylene Glycol Distearate | Galaxy Surfactants | 1.00 |
| | Cutina GMS V | Glyceryl Monostearate SE | BASF | 2.00 |
| | Ginol 16 (95%) | Cetyl Alcohol | Godrej | 1.00 |
| C | Synthetic Example 14 | | Momentive | 1.60 |
| | Element 14-5 | Dimethicone -5 cst | Momentive | 3.40 |
| | Sepigel305 | Polyacrylamide (and) C13-14 Isoparaffin (and) Laureth-7 | Seppic | 1.00 |
| | Euxyl ® PE 9010 | Phenoxyethanol (and) Ethylhexylglycerin | Schulke & Mayr | 0.70 |
| | Fragrance | Fragrance | Goldfield Fragrance Pvt Ltd. | 0.20 |
| | | | Total | 100.00 |

Formulation Example 4

Sunscreen.
Procedure:
 Phase A and Phase B ingredients were mixed separately,
 Slowly added Phase B to Phase A, and mixed them until homogeneous,
 Once the batch became homogeneous, poured product into suitable container.

TABLE 5

| Phase | Ingredient | INCI | Supplier | % w/w |
|---|---|---|---|---|
| A | Synthetic Example 14 | | Momentive | 25.00 |
| | SF 1202 | Cyclopentasiloxane | Momentive | 50.00 |
| B | Ethylhexyl salicylate | Ethylhexyl salicylate | BASF | 5.00 |
| | Ethylhexyl Methoxycinnamate | Ethylhexyl Methoxycinnamate | BASF | 10.00 |
| | | | Total | 100.00 |

Formulation Example 5

Sunscreen.
Procedure:
 The ingredient of Phase A and Phase B were weighed, mixed, and stirred separately with a regular lab stirrer until homogeneous,
 Slowly added Phase B to Phase A, and mixed then until homogeneous,
 Once the batch became homogeneous, poured product into suitable container.

TABLE 6

| Phase | Ingredient | INCI | Supplier | % w/w |
|---|---|---|---|---|
| A | Synthetic Example 14 | | | 25.00 |
| | SF 1202 | Cyclopentasiloxane | Momentive | 40.00 |
| B | Ethylhexyl salicylate | Ethylhexyl salicylate | BASF | 10.00 |
| | Ethylhexyl Methoxycinnamate | Ethylhexyl Methoxycinnamate | BASF | 15.00 |
| | Benzophenone 3 | Benzophenone 3 | BASF | 5.00 |
| | Octocrylene | Octocrylene | BASF | 5.00 |
| | | | Total | 100.00 |

Formulation Example 6

Cream.
Procedure:
The ingredients of Phase A and Phase B were weighed, mixed and stirred separately with a regular lab stirrer until homogeneous,
Slowly added Phase B to Phase A, and mixed then until homogeneous,
Once the batch became homogeneous, poured product into suitable container.

TABLE 7

| Phase | Ingredient | INCI | Supplier | % w/w |
|---|---|---|---|---|
| A | Synthetic Example 14 | | | 23.00 |
| | SF 1202 | Cyclopentasiloxane | Momentive | 54.50 |
| | SilSoft 034 | Caprylyl Methicone | Momentive | 2.00 |
| B | Water | Aqua | | 20.00 |
| | Euxyl 9010 | Phenoxyethanol (and) Ethylhexylglycerin | Schülke Inc | 0.50 |
| | | | Total | 100.00 |

Formulation Example 7

Clear glycerin gel cream.
Procedure:
The ingredients of Phase A and Phase B were weighed, mixed and stirred separately with a regular lab stirrer until homogeneous,
Slowly added Phase B to Phase A, and mixed then until homogeneous,
Once the batch became homogeneous, poured product into suitable container.

TABLE 8

| Phase | Ingredient | INCI | Supplier | % w/w |
|---|---|---|---|---|
| A | Synthetic Example 14 | | | 20.00 |
| | Element 14-5 | Dimethicone -5 cst | Momentive | 60.00 |
| B | Water | Aqua | | 10.00 |
| | Glycerin | Glycerin | Sigma Aldrich | 10.00 |
| | | | Total | 100.00 |

Formulation Example 8

Natural oil blend.
Procedure:
The ingredients of Phase A and Phase B were weighed, mixed and stirred separately with a regular lab stirrer until homogeneous,
Slowly added Phase B to Phase A, and mixed then until homogeneous,
Once the batch became homogeneous, poured product into suitable container.

TABLE 9

| Phase | Ingredient | INCI | Supplier | % w/w |
|---|---|---|---|---|
| A | Synthetic Example 14 | | | 25.00 |
| | SF 1202 | Cyclopentasiloxane | Momentive | 65.00 |
| B | Almond Oil | Prunus Amygdalus Dulcis (Sweet Almond) Oil | Sigma Aldrich | 5.00 |
| | Jojoba Oil | Simmondsia Chinensis (Jojoba) Seed Oil | Sigma Aldrich | 5.00 |
| | | | Total | 100.00 |

Formulation Example 9

Roll-on anti-perspirant.
Procedure:
The ingredients of Phase A and Phase B were weighed, mixed and stirred separately with a regular lab stirrer until homogeneous,
Slowly added Phase B to Phase A, and mixed then until homogeneous,
Once the batch became homogeneous, poured product into suitable container.

TABLE 10

| Phase | Ingredient | INCI | Supplier | % w/w |
|---|---|---|---|---|
| A | Synthetic Example 14 | | | 28.06 |
| | SF 1202 | Cyclopentasiloxane | Momentive | 67.46 |
| B | Polyaluminium chloride | Polyaluminium chloride | Sigma Aldrich | 2.24 |
| | Water | Aqua | | 2.24 |
| | | | Total | 100.00 |

Formulation Example 10

Hair Serum.
Procedure:
Mixed all the ingredients until the mixture became uniform.

TABLE 11

| Phase | Ingredient | INCI | Supplier | % w/w |
|---|---|---|---|---|
| A | Synthetic Example 14 | | | 20.00 |
| | SF 1202 | Cyclopentasiloxane | Momentive | 78.00 |
| | Olive Oil | Olea Europaea Fruit Oil (Olive Oil) | Sigma Aldrich | 2.00 |
| | | | Total | 100.00 |

Formulation Example 11

Foundation mousse.

Procedure:

The ingredients of Phase A and Phase B were weighed, mixed and stirred separately with a regular lab stirrer until homogeneous, Slowly added Phase B to Phase A, and mixed then until homogeneous, Once the batch became homogeneous, poured product into suitable container.

TABLE 12

| Phase | Ingredient | INCI | Supplier | % w/w |
|---|---|---|---|---|
| A | Synthetic Example 14 | | | 20.00 |
| | SF 1202 | Cyclopentasiloxane | Momentive | 60.50 |
| B | Silshine 151 | Phenylpropyldimethylsiloxysilicate | Momentive | 6.50 |
| | Tospearl 2000B | Polymethylsilsesquioxane | Momentive | 5.00 |
| | Titanium Dioxide | Titanium dioxide (CI 77891) | Koel Colors | 7.00 |
| | Iron oxide Yellow | CI 77492 (Yellow Iron Oxide) | Koel Colors | 0.60 |
| | Iron Oxide Red | CI 77491 (Red Iron Oxide) | Koel Colors | 0.34 |
| | Iron Oxide Black | CI 77499 (Black Iron oxide) | Koel Colors | 0.06 |
| | | | Total | 100.00 |

Formulation Example 12

Lipstick.

Procedure:

The ingredients of Phase A were weighed, and mixed until homogeneous at a temperature between 75 to 80° C., The ingredients of Phase B were mixed, and added to Phase A, and stirred at a temperature between 75 to 80° C. until homogeneous, Poured the heated mixer into a lipstick mold, and let it cool, Once cooled, the lipstick formed was taken out from the mold.

TABLE 13

| Phase | Ingredient | INCI | Supplier | % w/w |
|---|---|---|---|---|
| A | Beeswax | *Cera Alba* (Beeswax) | Sigma Aldrich | 5.00 |
| | Candelila Wax | *Candelilla cera* | Sigma Aldrich | 4.00 |
| | Carnauba Wax | *Copernicia Cerifera* (Carnauba) Wax | Sigma Aldrich | 5.00 |
| | Ozokerite | Ozokerite | Sigma Aldrich | 5.00 |
| | Sophium MC 30 | Hydrogenated polyisobutene | SEPPIC | 5.00 |
| | Tocopheryl acetate | Tocopheryl acetate | Sigma Aldrich | 1.00 |
| | Silshine 151 | Phenylpropyldimethylsiloxysilicate | Momentive | 8.00 |
| B | Synthetic Example 14 | | | 15.00 |
| | Isopopyl Palmitate | Isopopyl Palmitate | Croda | 47.50 |
| | Col Mud Lithol Rubine B | PIGMENT RED 57:1 | Koel Colors | 2.50 |
| | Silver Pigment | | Merck | 2.00 |
| | | | Total | 100.00 |

What is claimed is:

1. A composition comprising a polymer having branched silicone substituted by at least one alkylcarboxy group in a free or salt form, wherein said branched silicone is cross-linked with an alkenyl functional cross-linker, wherein an average number of alkylcarboxy substitutions per silicone is between 1 and 60 and an average number of crosslinks between branched silicones is between 1 and 30.

2. The composition of claim 1, wherein the average number of alkylcarboxy substitutions per silicone is between 1 and 15.

3. The composition of claim 1, wherein the average number of crosslinks between branched silicones is between 1 and 15.

4. The composition of claim 1, wherein the polymer is prepared by a method comprising (a) reacting
  i. a Si-H functional compound of formula (I):

$$[SiO_{4/2}]_a[R^1SiO_{3/2}]_b[R^2MeSiO_{2/2}]_c[HMeSiO_{2/2}]_d[R^3Me_2SiO_{1/2}]_e[HMe_2SiO_{1/2}]_f \quad (I)$$

wherein
  $R^1$ is hydrogen, an aliphatic, aromatic, or fluoro monovalent hydrocarbon having from 1 to 60 carbon atoms;
  $R^2$ and $R^3$ are each an aliphatic, aromatic, or fluoro monovalent hydrocarbon having from 1 to 60 carbon atoms; and
  $a \geq 0$, $b \geq 0$, $a+b \geq 1$, $c \geq 0$, $d \geq 0$, $e \geq 0$, $f \geq 1$, and $d+f \geq 2$;

ii. a carboxy functional olefin of formula (II):

wherein
R' is hydrogen or —Si(R$^a$)$_3$ wherein R$^a$ is an aliphatic monovalent hydrocarbon;
n is 0≤n≤30; and
iii. a silicone based alkenyl functional cross-linker of formula (III) and/or a non-silicone based alkenyl functional cross-linker of formula (IV):

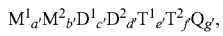  (III)

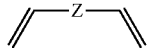  (IV)

wherein:
M$^1$=R$^4$R$^5$R$^6$SiO$_{1/2}$;
M$^2$=R$^7$R$^8$R$^9$SiO$_{1/2}$;
D$^1$=R$^{10}$R$^{11}$SiO$_{2/2}$;
D$^2$=R$^{12}$R$^{13}$SiO$_{2/2}$;
T$^1$=R$^{14}$SiO$_{3/2}$;
T$^2$=R$^{15}$SiO$_{3/2}$;
Q=SiO$_{4/2}$;
wherein
R$^5$, R$^6$, R$^7$, R$^8$, R$^9$, R$^{11}$, R$^{12}$, R$^{13}$, and R$^{15}$ are independently an aliphatic, aromatic, or fluoro monovalent hydrocarbon having from 1 to 60 carbon atoms;
R$^4$, R$^{10}$, and R$^{14}$ are each a monovalent radical containing at least one terminal olefin bond;
a', b', c', d', e', f' and g' are independently zero or a positive integer, such that 2≤a'+b'+c'+d'+e'+f'+g'≤6000 and when a'+c'+e'=2, d+f>2 or when d+f=2, a'+c'+e'>2; and
Z is —(CHR$^{16}$)$_m$— or —(CH$_2$CHR$_{17}$O)$_k$—, wherein m and k are positive integers, such that 1≤m≤60 and 1≤k≤500, and R$^{16}$ and R$^{17}$ are independently hydrogen or monovalent hydrocarbon having from 1 to 60 carbon atoms; and
(b) optionally deprotecting the reaction product of step (a) to replace the —Si(R$^a$)$_3$ group with a hydrogen.

5. The composition of claim 4, wherein R$^1$ is an aliphatic, aromatic, or fluoro monovalent hydrocarbon.

6. The composition of claim 4, wherein one or more of R$^2$ and R$^3$ is a C$_1$-C$_{30}$ monovalent hydrocarbon.

7. The composition of claim 4, wherein R$^a$ is a C$_1$-C$_{12}$ group.

8. The composition of claim 4, wherein one or more R$^5$, R$^6$, R$^7$, R$^8$, R$^9$, R$^{11}$, R$^{12}$, R$^{13}$, and R$^{15}$ is a C$_1$-C$_{30}$ monovalent hydrocarbon.

9. The composition of claim 4, wherein one or more of R$^5$, R$^6$, R$^7$, R$^8$, R$^9$, R$^{11}$, R$^{12}$, R$^{13}$, and R$^{15}$ is an aromatic monovalent hydrocarbon.

10. The composition of claim 4, wherein one or more of R$^5$, R$^6$, R$^7$, R$^8$, R$^9$, R$^{11}$, R$^{12}$, R$^{13}$, and R$^{15}$ is a fluoro monovalent hydrocarbon.

11. The composition of claim 1, wherein the polymer is in a free form.

12. The composition of claim 1, wherein the polymer is in a salt form.

13. A method for preparing a polymer having branched silicone comprising reacting:
i. a Si-H functional compound of formula (I):

[SiO$_{4/2}$]$_a$[R$^1$SiO$_{3/2}$]$_b$[R$^2$MeSiO$_{2/2}$]$_c$[HMeSiO$_{2/2}$]$_d$ [R$^3$Me$_2$SiO$_{1/2}$]$_e$[HMe$_2$SiO$_{1/2}$]$_f$  (I)

wherein
R$^1$ is hydrogen, an aliphatic, aromatic, or fluoro monovalent hydrocarbon having from 1 to 60 carbon atoms;
R$^2$ and R$^3$ are each an aliphatic, aromatic, or fluoro monovalent hydrocarbon having from 1 to 60 carbon atoms; and
a≥0, b≥0, a+b≥1, c≥0, d≥0, e≥0, f≥1, and d+f≥2;
ii. a carboxy functional olefin of formula (II):

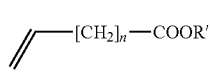  (II)

wherein
R' is hydrogen or —Si(R$^a$)$_3$ wherein R$^a$ is an aliphatic monovalent hydrocarbon;
n is 0≤n≤30; and
iii. a silicone based alkenyl functional cross-linker of formula (III) and/or a non-silicone based alkenyl functional cross-linker of formula (IV):

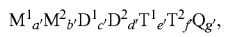  (III)

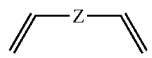  (IV)

wherein:
M$^1$=R$^4$R$^5$R$^6$SiO$_{1/2}$;
M$^2$=R$^7$R$^8$R$^9$SiO$_{1/2}$;
D$^1$=R$^{10}$R$^{11}$SiO$_{2/2}$;
D$^2$=R$^{12}$R$^{13}$SiO$_{2/2}$;
T$^1$=R$^{14}$SiO$_{3/2}$;
T$^2$=R$^{15}$SiO$_{3/2}$;
Q=SiO$_{4/2}$;
wherein
R$^5$, R$^6$, R$^7$, R$^8$, R$^9$, R$^{11}$, R$^{12}$, R$^{13}$, and R$^{15}$ are independently an aliphatic, aromatic, or fluoro monovalent hydrocarbon having from 1 to 60 carbon atoms;
R$^4$, R$^{10}$, and R$^{14}$ are each a monovalent radical containing at least one terminal olefin bond;
a', b', c', d', e', f' and g' are independently zero or a positive integer, such that 2≤a'+b'+c'+d'+e'+f'+g'≤6000 and when a'+c'+e'=2, d+f>2 or when d+f=2, a'+c'+e'>2;
Z is —(CHR$^{16}$)$_m$— or —(CH$_2$CHR$_{17}$O)$_k$—, wherein m and k are positive integers, such that 1≤m≤60 and 1≤k≤500, and R$^{16}$ and R$^{17}$ are independently hydrogen or monovalent hydrocarbon having from 1 to 60 carbon atoms; and
wherein an average number of crosslinks between branched silicones is between 1 and 30.

14. The method of claim 13, wherein the method further comprises deprotecting the reaction product to replace the —Si(R$^a$)$_3$ group with a hydrogen.

15. The method of claim 13, wherein the polymer is in a free form.

16. The method of claim 13, wherein the polymer is in a salt form.

17. A method of preparing a polymer having branched silicone comprising deprotecting a reaction product of
  i. a Si-H functional compound of formula (I):

$$[SiO_{4/2}]_a[R^1SiO_{3/2}]_b[R^2MeSiO_{2/2}]_c[HMeSiO_{2/2}]_d[R^3Me_2SiO_{1/2}]_e[HMe_2SiO_{1/2}]_f \quad (I)$$

wherein
   $R^1$ is hydrogen, an aliphatic, aromatic, or fluoro monovalent hydrocarbon having from 1 to 60 carbon atoms;
   $R^2$ and $R^3$ are each an aliphatic, aromatic, or fluoro monovalent hydrocarbon having from 1 to 60 carbon atoms; and
   $a \geq 0$, $b \geq 0$, $a+b \geq 1$, $c \geq 0$, $d \geq 0$, $e \geq 0$, $f \geq 1$, and $d+f \geq 2$;
  ii. a carboxy functional olefin of formula (II):

$$\text{//---}[CH_2]_n\text{---}COOR' \quad (II)$$

wherein
   R' is hydrogen or —Si(R$^a$)$_3$ wherein R$^a$ is an aliphatic monovalent hydrocarbon;
   n is $0 \leq n \leq 30$; and
  iii. a silicone based alkenyl functional cross-linker of formula (III) and/or a non-silicone based alkenyl functional cross-linker of formula (IV):

$$M^1_{a'}M^2_{b'}D^1_{c'}D^2_{d'}T^1_{e'}T^2_{f'}Q_{g'} \quad (III)$$

$$\text{//---Z---}\backslash\backslash \quad (IV)$$

wherein:
   $M^1 = R^4R^5R^6SiO_{1/2}$;
   $M^2 = R^7R^8R^9SiO_{1/2}$;
   $D^1 = R^{10}R^{11}SiO_{2/2}$;
   $D^2 = R^{12}R^{13}SiO_{2/2}$;
   $T^1 = R^{14}SiO_{3/2}$;
   $T^2 = R^{15}SiO_{3/2}$;
   $Q = SiO_{4/2}$;
   wherein
   $R^5$, $R^6$, $R^7$, $R^8$, $R^9$, $R^{11}$, $R^{12}$, $R^{13}$, and $R^{15}$ are independently an aliphatic, aromatic, or fluoro monovalent hydrocarbon having from 1 to 60 carbon atoms;
   $R^4$, $R^{10}$, and $R^{14}$ are each a monovalent radical containing at least one terminal olefin bond;
   a', b', c', d', e', f' and g' are independently zero or a positive integer, such that $2 \leq a'+b'+c'+d'+e'+f'+g' \leq 6000$ and when $a'+c'+e'=2$, $d+f>2$ or when $d+f=2$, $a'+c'+e'>2$;
   Z is —(CHR$^{16}$)$_m$— or —(CH$_2$CHR$_{17}$O)$_k$—, wherein m and k are positive integers, such that $1 \leq m \leq 60$ and $1 \leq k \leq 500$, and $R^{16}$ and $R^{17}$ are independently hydrogen or monovalent hydrocarbon having from 1 to 60 carbon atoms; and
   wherein an average number of crosslinks between branched silicones is between 1 and 30.

18. The method of claim 13, wherein $R^1$ is an aliphatic, aromatic, or fluoro monovalent hydrocarbon.

19. The method of claim 13, wherein one or more of $R^2$ and $R^3$ is a $C_1$-$C_{30}$ monovalent hydrocarbon.

20. The method of claim 13, wherein R$^a$ is a $C_1$-$C_{12}$ group.

21. The method of claim 13, wherein one or more of $R^5$, $R^6$, $R^7$, $R^8$, $R^9$, $R^{11}$, $R^{12}$, $R^{13}$, and $R^{15}$ is a $C_1$-$C_{30}$ monovalent hydrocarbon.

22. A personal care composition comprising:
   (a) the composition of claim 1; and
   (b) one or more personal care components.

23. The composition of claim 4, wherein (ii) is performed before (iii).

24. The method of claim 13, wherein (ii) is performed before (iii).

25. The composition of claim 4, wherein a=10, b=c=d=e=0, f=12, and n=8.

26. The composition of claim 4, wherein a=0, b=1, c=d=e=0, f=3, and n=8.

* * * * *